(12) United States Patent
Koch et al.

(10) Patent No.: US 6,610,532 B2
(45) Date of Patent: Aug. 26, 2003

(54) INTRACELLULAR INHIBITORS OF GQ PROTEIN SIGNALING

(75) Inventors: Walter J. Koch, Durham, NC (US); Robert J. Lefkowitz, Durham, NC (US); Shahab A. Akhter, Durham, NC (US); Louis M. Luttrell, Durham, NC (US); Howard Rockman, Chapel Hill, NC (US)

(73) Assignee: Duke University, Durham, NC (US)

( * ) Notice: Subject to any disclaimer, the term of this patent is extended or adjusted under 35 U.S.C. 154(b) by 177 days.

(21) Appl. No.: 09/121,814

(22) Filed: Jul. 24, 1998

(65) Prior Publication Data

US 2002/0045248 A1 Apr. 18, 2002

Related U.S. Application Data

(60) Provisional application No. 60/053,659, filed on Jul. 24, 1997.

(51) Int. Cl.[7] .................. A61K 48/00; A61K 9/127; C07H 21/04; C12N 15/74
(52) U.S. Cl. .................. 435/320.1; 424/93.2; 424/450; 536/23.1
(58) Field of Search .................. 435/320.1, 325; 514/44; 424/93.2, 450; 536/23.1

(56) References Cited

U.S. PATENT DOCUMENTS

| | | |
|---|---|---|
| 5,082,779 A | 1/1992 | Rottman et al. |
| 5,175,383 A | 12/1992 | Leder |
| 5,175,384 A | 12/1992 | Krimpenfort |
| 5,175,385 A | 12/1992 | Wagner et al. |
| 5,624,936 A | 4/1997 | deSolms |
| 5,981,487 A | 11/1999 | Koch |

FOREIGN PATENT DOCUMENTS

| | | |
|---|---|---|
| EP | 0 351 921 | 1/1990 |
| EP | 0 453 119 | 10/1991 |
| WO | WO 92/07070 | 4/1992 |

OTHER PUBLICATIONS

Friedmann, T. Overcoming the obstacles to gene therapy. Sci. Am. Jun. 1997, pp. 96–101.*
Orkin and Motulsky. Report and recommendations of the panel to assess the NIH investment in research on gene therapy, Dec. 1995.*
Verma et al. Gene therapy—promises, problems and prospects. Nature 389: 239–242, Sep. 1997.*
Crystal, "Transfer of Genes to Humans: Early Lessons and Obstacles to Success", Science 270:404–410 (1995).
Marshall, "Less Hype, More Biology Needed for Gene Therapy", Science 270:1751 (1995).
Coghlan, "Gene dream fades away", New Scientist 148:14–15 (1995).
Günsburg et al, "Virus vector design in gene therapy", Molecular Medicine Today pp. 410–417 (1995).
Foecking et al, "Powerful and versatile enhancer–promoter unit for mammalian expression vectors", Gene 45:101–105 (1986).
Koch et al, "Cellular Expression of the Carboxyl Terminus of a G Protein–coupled Receptor Kinase Attenuates G$\beta\gamma$–mediated Signaling", J. Biological Chem. 269:6193–6197 (1994).
Lee et al, "Cardiac and Pulmonary Replacement", J. Thoracic Cardiovascular Surgery 111(1):246–252 (1996).
Fuller et al, "Genetic Engineering of Cardiac Muscle Cells: In Vitro and In Vivo", Genetic Engineering 16:17–27 (1994).
Luckow et al, "CAT constructions with multiple unique restriction sites for the functional analysis of eukaryotic promoters and regulatory elements", Nucleic Acids Research 15(13):5490 (1987).
Ngo et al, "Computational Complexity, Protein Structure Prediction, and the Levinthal Paradox", The Protein Folding Problem and Tertiary Structure Prediction, K. Merz, Jr. and S. Le Grand, Editors, Birkhauser Bost Inc., pp. 491–495 (1994).
Dillon, "Regulating gene expression in gene therapy", TibTech 11:167–173 (1993).
Rigby, "Gene therapy: a long and winding road", Current Opinion in Genetics and Development 5:397–398 (1995).
Orkin et al, "Report and Recommendations of the Panel to Assess the NIH Investment in Research on Gene Therapy", pp. 1–50, Dec. 7, 1995.
Benovic et al, "cDNA Cloning and Chromosomal Localization of the Human $\beta$–Adrenergic Receptor Kinase", FEBS 283(1):122–126 (1991).
Bertin et al, "Atrial Overexpression of B1–AR in Transgenic Mice. A New Potential Pharmacological Model", Cardiovascular Drugs and Therapy 7 (Suppl. 2):465 (1993).
Gaudin et al, Overexpression of Gs$\alpha$ Protein the Haeart of Transgenic Mice, Clinical Res. 41(2):145a (1993).
Schmidt et al, "The Cytomegalovirus Enhancer: a Pan–Active Control Element in Transgenic Mice", Molecular and Cellular Biology 10:4406–4411 (1990).
Touhara et al, "Mutational Analysis of the Pleckstrin Homology Domain of the $\beta$–Adrenergic Receptor Kinase", The Journal of Biological Chemistry 270(28):17000–17005 (1995).
Milano et al, "Enhanced Myocardial Function in Transgenic Mice Overexpressing the $\beta_2$–Adrenergic Receptor", Science 264:582–586 (1994).
Seachrist, L., "Gene Transfer to Spark a Failing Heart", Science 264:507–508 (1994).

(List continued on next page.)

*Primary Examiner*—Anne-Marie Baker
(74) *Attorney, Agent, or Firm*—Nixon & Vanderhye P.C.

(57) ABSTRACT

The present invention relates, in general, to myocardial hypertrophy and, in particular, to agents that inhibit cardiac Gq-coupled receptor signaling and to methods of inhibiting myocardial hypertrophy using same.

7 Claims, 10 Drawing Sheets

OTHER PUBLICATIONS

Koch et al, "Cardiac Function in Mice Overexpressing the β–Adrenergic Receptor Kinase or a βARK Inhibitor", Science 268:1350–1353 (1995).

Kaufman, Randal J., "Expression of Proteins in Mammalian Cells", Current Protocols in Molecular Biology, Supplement 14, Section III, Unit 16.12.1–16.12.6 (1994).

Aruffo, A., "Transient Expression of Proteins Using COS Cells", Current Protocols in Molecular Biology, Supplemental 14, Section III, Unit 16.13.1–16.13.7 (1991).

Subramaniam et al, "Tissue–specific Regulation of the α–Myosin Heavy Chain Gene Promoter in Transgenic Mice", The Journal of Biological Chemistry 266(36):24613–24620 (1991).

Shubeita et al, "Transcriptional activation of the cardiac myosin light chain 2 and atrial natriuretic factor genes by protein kinase C in neonatal rat ventricular myocytes", Proc. Natl. Acad. Sci. USA 89:1305–1309 (1992).

Inglese et al, "Functionally active targeting domain of the β–adrenergic receptor kinase: An inhibitor of Gβγ–mediated stimulation of type II adenylyl cyclase", Proc. Natl. Acad. Sci. USA 91:3637–3641 (1994).

Irani et al, "Ras Proteins Regulate Multiple Mitogenic Pathways in A10 Vascular Smooth Muscle Cells", Biochemical and Biophysical Research Communications 202(3):1252–1258 (1994).

Laugwitz et al, "Characterization and inhibition of β–adrenergic receptor kinase in intact myocytes", Cardiovascular Research 35:324–333 (1997).

Xu et al, "The N terminus of phosducin is involved in binding of βγ subunits of G protein", Proc. Natal. Acad. Sci. USA 92:2086–2090 (1995).

Akhter et al, "Restoration of β–adrenergic signaling in failing cardiac ventricular myocytes via adenoviral–mediated gene transfer", Proc. Natl. Acad. Sci. USA 94:1–6 (1997).

Lilly et al, "Intracoronary Administration of Adenovirus for Gene Transfer inot Adult Rabbit Myocardium", Surgical Forum 47:279–281 (1996).

Drazner et al, "Potentiation of β–Adrenergic Signaling by Adenoviral–mediated Gene Transfer in Adult Rabbit Ventricular Myocytes", J. Clin. Invest. 99(2):288–296 (1997).

Hawes et al, "Determination of the $G_{\beta\gamma}$–binding Domain of Phosducin", The Journal of Biological Chemistry 269(47):29825–29830 (1994).

Dixon et al, "Ligand binding to the β adrenergic receptor involves its rhodopsin–like core", Nature 326:73 (1987).

Boshart et al, "A very strong enhancer is located upstream of an intermediate early gene of human cytomegalovirus", Cell 41:521 (1985).

Fowler et. al., "Assessment of the β–adrenergic receptor pathway in the intact failing human heart: . . . ," Circulation, vol. 74, No. 6, Dec. 1986, pp. 1290–1302.

Ungerer et al., "Altered Expression of β–Adrenergic Receptor Kinase and $\beta_1$–Adrenergic . . . ," Circulation, vol. 87, 1993, pp. 454–463.

Koch et al., "The Binding Site for the βτ Subunits of Heterotrimeric G Proteins . . . ," The Journal of Biological Chemistry. vol. 268. No. 11, Apr. 15, 1993, pp. 8256–8260.

Benovic et al., "β–Adrenergic Receptor Kinase: Primary Structure Delineates a Multigene Family," Science, vol. 246, Oct. 13, 1989, pp. 235–240.

Hausdorff et al., "Turning off the signal: densensitization of a β–adrenergic receptor function," The FASEB Journal, vol. 4, Aug. 1990, pp. 2881–2889.

Lohse et al., "Multiple Pathways of Rapid $\beta_2$–Adrenergic Receptor Desensitization," The Journal of Biological Chemistry, vol. 265, No. 6, Feb. 25, 1990, pp. 3202–3209.

Inglese et al., "Structure and Mechanism of the G Protein–coupled Receptor Kinases," The Journal of Biological Chemistry, vol. 268, No. 32, Nov. 15, 1993, pp. 23735–23738.

Ng et al., "Cardiac–Myosin Heavy Chain mRNA Expression and Myocardial Function in the Mouse Heart," Circulation Research, vol. 68, No. 6, Jun. 1991, pp. 1742–1750.

Medford et al., "Molecular Mechanisms Regulating VCAM–1, ICAM–1 and E–Selectin Gene Expression in Human Aortic Smooth Muscle Cells", Clinical Research, vol. 41, No. 2, 1993, p. 145A.

Pitcher et al., "Role of βτ Subunits of G Proteins in Targeting the β–Adrenergic . . . ", Science, vol. 257, Aug. 28, 1992, pp. 1264–1267.

Yatani et al., "A G Protein Directly Regulates Mammalian Cardiac Calcium Channels," Science, vol. 238, Nov. 1987, pp. 1288–1292.

Kolbilka et al., "cDNA for the human $\beta_2$–adrenergic receptor: A protein with multiple . . . ," Proc. Natl. Acad. Sci. USA, vol. 84, Jan. 1987, pp. 46–50.

Kass–Eisler et al., "Quantitative determination of adenovirus–mediated gene delivery . . . ," Proc. Natl. Acad. Sci. USA, vol. 90, Dec. 1993, pp. 11498–11502.

Stratford–Perricaudet et al., "Widespread Long–term Gene Transfer to Mouse Skeletal . . . ," J. Clin. Invest., vol. 90, Aug. 1992, pp. 626–630.

Guzman et al., "Efficient Gene Transfer into Myocardium by Direct Injection of Adenovirus Vectors," Circulation Research, vol. 73, 1993, pp. 1202–1207.

Bertin et al., "Specific atrial overexpression of G protein coupled human $\beta_1$ adrenoceptors . . . ," Cardiovascular Research, vol. 27, 1993, pp. 1606–1612.

Metzger et al, "Skeletal troponin C reduces contractile sensitivity to acidosis in cardiac . . . ," Proc. Natl. Acad. Sci. USA, vol. 90, Oct. 1993, pp. 9036–9040.

Ren et al., "Constitutively Active Mutants of the $\alpha_2$–Adrenergic Receptor," The Journal of Biological Chemistry, vol. 268, No. 22, Aug. 5, 1993, pp. 16483–16487.

Pauletto et. al., "Propranolol–induced changes in ventricular isomyosin composition in the rat," American Heart Journal, vol. 109, Jun. 1985, pp. 1269–1273.

Bristow et al., "Decreased Catecholamine Sensitivity and β–Adrenergic–Receptor . . . ," The New England Journal of Medicine, vol. 307, No. 4, Jul. 22, 1982, pp. 205–211.

Bristow et al., β–Adrenergic Function in Heart Muscle Disease and Heart Failure, J. Mol. Cell. Cardiol. 17 (Supp. 2), 1985, pp. 41–52.

Bristow et al., "β–Adrenergic Pathways in Nonfailing and Failing Human Ventricular Myocardium," Circulation, vol. 82 (Suppl. I), 1990, pp. I–12–I–25.

LaMorte et al, Gq– and Ras–dependent Pathways Mediate Hypertrophy of Neonatal Rat Ventricular Myocytes following $\beta_1$–Adrenergic Stimulation, The Journal of Biological Chemistry 269(18):13490–13496 (1994).

Sah et al, "Rho Is Required for $G\alpha_q$ and $\alpha_1$–Adrenergic Receptor Signaling in Cardiomyocytes", The Journal of Biological Chemistry, 271(49):31185–31190 (1996).

Meij, "Regulation of G protein function: Implications for heart disease", Molecular and Cellular Biochemistry 157:31–38 (1996).

D'Angelo et al, "Transgenic $G\alpha q$ overexpression induces cardiac contractile failure in mice", Proc. Natl. Acad. Sci. USA 94:81212–8126 (1997).

Sakata et al, "Decompensation of Pressure–Overload Hypertrophy in $G\alpha q$–Overexpressing Mice", Journal of the American Heart Association Basic Science Reports 97(15):1488–1495 (1998).

Akhter et al, "Targeting the Receptor–Gq Interface to Inhibit in Vivo Pressure Overload Myocardial Hypertrophy", Science 280:574–577 (1998).

* cited by examiner

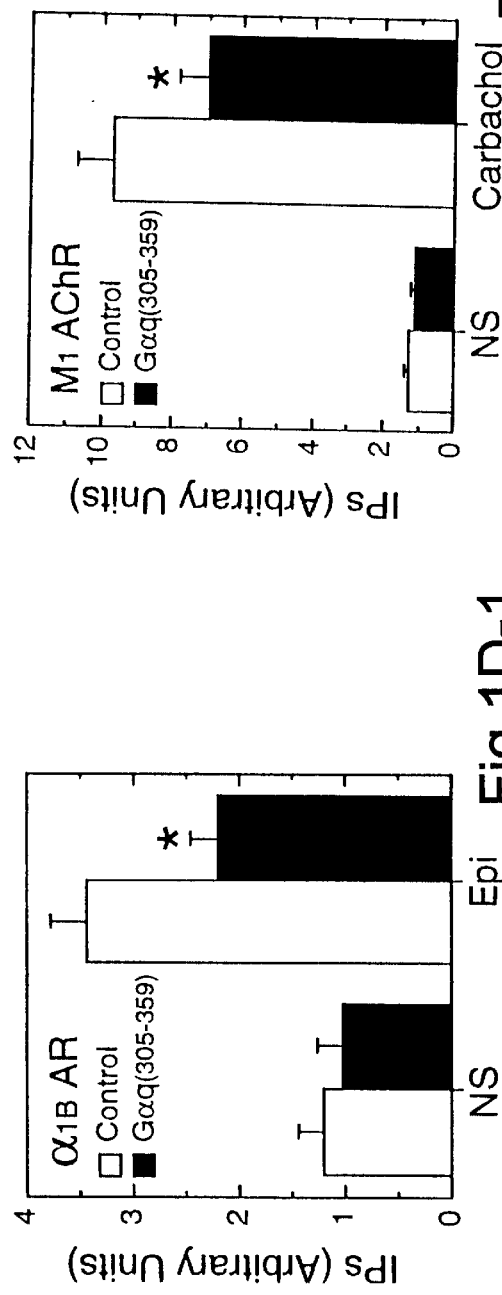
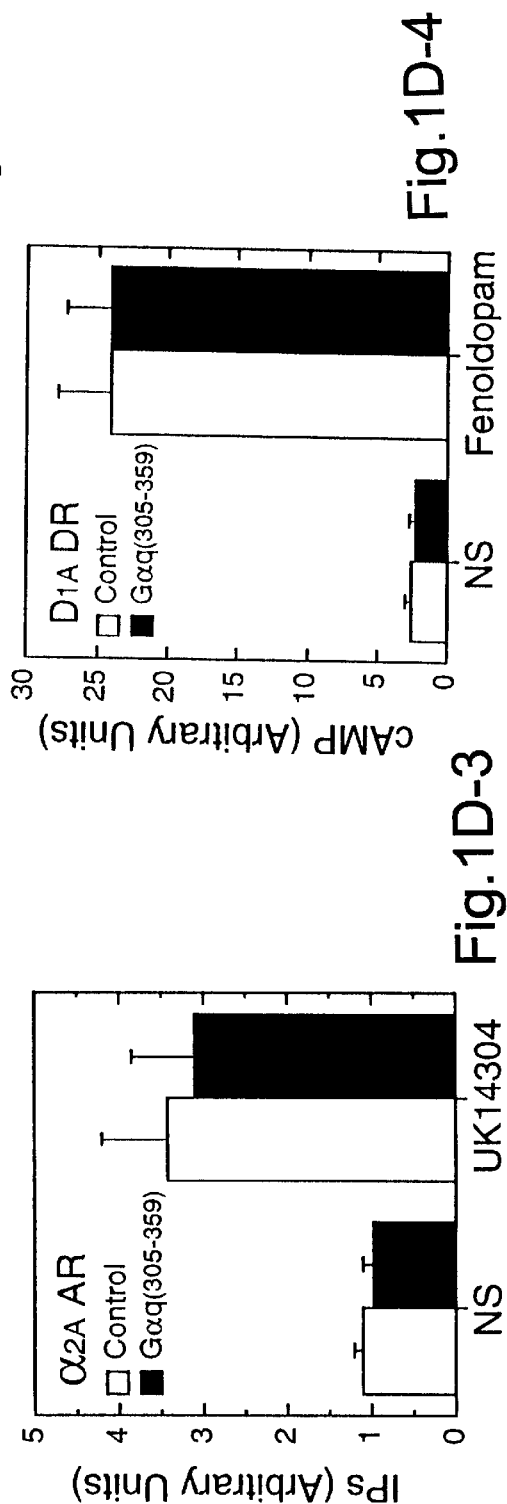

SEQUENCE LISTING

<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence:Primer

<400> SEQUENCE: 1
gccgccacca tg                                                          12

INTRACELLULAR INHIBITORS OF GQ PROTEIN SIGNALING

This application claims the benefit of U.S. Provisional Application No. 60/053,659, filed Jul. 24, 1997.

This invention was made with Government support under Grant No. HL09436-02 awarded by the National Institutes of Health and NC-96-65-67 awarded by the American Heart Association. The Government has certain rights in the invention.

TECHNICAL FIELD

The present invention relates, in general, to myocardial hypertrophy and, in particular, to agents that inhibit cardiac Gq-coupled receptor signaling and to methods of inhibiting myocardial hypertrophy using same.

BACKGROUND

Myocardial hypertrophy is an adaptive response to a variety of mechanical and hormonal stimuli and represents an initial step in the pathogenesis of many cardiac diseases which ultimately progress to ventricular failure. Due to the high mortality associated with heart failure, there is strong interest in identifying regulatory molecular determinants which lead to myocardial hypertrophy and subsequently to the transition to failure. Several disease conditions can trigger the non-failing ventricle to develop increased wall thickness as an initial compensatory mechanism to meet the heightened demands placed on the pump. In man, this situation can arise in some cardiovascular disease states including hypertension. The mechanisms by which cardiac hypertrophy is initiated and how this condition eventually progresses to heart failure are poorly understood.

The heart is unique in that it is composed of terminally differentiated myocytes which respond to hypertrophic stimuli by increasing in size rather than number (Chien et al, FASEB J. 5:3037 (1991)). Utilizing cultured neonatal cardiac myocytes, several independent signaling pathways have been implicated in the activation of the hypertrophic response in vitro (Chien et al. FASEB J. 5:3037 (1991). The hypertrophy seen in vitro involves an increase in cellular size and volume, differential expression of various contractile proteins, and reactivation of an embryonic gene program which includes ventricular induction of atrial natriuretic factor (ANF), skeletal a-actin, and b-myosin heavy chain. Candidate signaling molecules for the initiation of hypertrophy have been identified including $p21^{ras}$ (ras) (Thorburn et al, J. Biol. Chem. 268:2244 (1993)), although hypertrophy of myocytes in vitro can also occur in a ras-independent manner (LaMorte et al, J. Biol. Chem. 269:13490(1994)). The heterotrimeric guanine nucleotide binding (G) protein, Gq, is thought to be important in this process since various ligands (i.e. phenylephrine, angiotensin II, and endothelin I) that activate Gq-coupled receptor molecules can trigger hypertrophic responses in cultured myocytes (Sadoshima et al, Cell 95:977 (1993), Simpson, J. Clin. Invest. 72:732 (1983); Shubeita et al, J. Biol. Chem. 265:20555 (1990)).

Receptors that stimulate Gq are members of the G protein-coupled receptor family which share conserved seven transmembrane topography. The binding of agonists induces conformational changes in the receptor molecule which cause its intracellular domains to interact with the carboxyl terminal portion of the a-subunit of G proteins (Neer et al, Cell 80:249 (1995)). It has been previously reported that cellular expression of the third intracellular domain (3i) of the $a_{1B}$-adrenergic receptor (AR) in vitro antagonizes $a_{1B}$-AR-mediated signal transduction, apparently through competition between the 3i peptide and the activated receptor for binding sites on Gaq (Luttrell et al, Science 259:1453 (1993)). Other in vitro studies have demonstrated that peptides derived from the carboxyl terminus of Gas (Palm et al. FEBS Lett. 261:294 (1990)) and $Gai_2$ (Okamato et al, J. Biol. Chem. 269:13756 (1994)) can block in vitro receptor-mediated G protein signaling.

The present invention results from studies demonstrating, in vivo, the importance of myocardial Gq-coupled signaling in the initiation of ventricular hypertrophy. This demonstration makes possible novel therapeutic strategies for preventing hypertrophy and the transition to heart failure.

SUMMARY OF THE INVENTION

The present invention relates to agents that inhibit cardiac Gq-coupled receptor signaling. The invention further relates to a method of inhibiting maladaptive ventricular hypertrophy associated with various forms of cardiac disease in transition to failure, which method utilizes such agents. The invention further relates to a method of inhibiting vascular smooth muscle proliferation and migration, which method also utilizes inhibitors of Gq-coupled receptor signaling.

Objects and advantages of the invention will be clear from the description that follows.

BRIEF DESCRIPTION OF THE DRAWINGS

FIGS. 1A–D. Selective inhibition of Gq-receptor coupling by transient expression of the Gaq(305–359) peptide minigene in COS-7 cells. FIG. 1A. Schematic representation of Gaq minigene constructs. Shaded bars represent the relative position of the peptide sequences encoded by the Gaq(305–359) and Gaq(1–54) minigene constructs compared to the linear sequence of the Gaq-subunit. The cDNA encoding each of the peptides was cloned into a minigene construct depicted schematically in the lower panel. FIG. 1B. Expression of intact Gaq and Gaq(305–359) peptide in transiently transfected COS-7 cells. COS-7 cells were transiently transfected with plasmid DNA encoding either empty vector, the Gaq(305–359) minigene, or Gaq and expression of the Gaq-carboxy-terminal epitope was determined by protein immunoblotting of whole cell detergent lysates. FIG. 1C. Effect of coexpressed intact Gaq or Gaq-derived peptide minigenes on $a_{1B}$-AR-mediated IP production. COS-7 cells were transiently cotransfected with plasmid DNA encoding the $a_{1B}$-AR (0.01 to 1.0 mg DNA/well) plus either intact Gaq, the Gaq(305–359) peptide (2.0 mg/well), or the Gaq (1–54) peptide. Basal (solid circles) and epinephrine-stimulated (solid-squares) inositol phosphate (IP) production was determined as described (solid lines). Basal (open circles) and epinephrine-stimulated (open squares) responses from control cells transfected with the receptor plasmid plus empty vector are shown in each panel (broken lines). Data are presented in arbitrary units such that one unit equals the basal level of inositol phosphates measured in cells transfected with empty vector alone. Data shown represent mean ±SEM values for triplicate determinations in a single experiment which was reproduced four times.

FIG. 1D. Specificity of Gaq(305–359) peptide-induced inhibition of G protein-coupled receptor-mediated signaling. COS-7 cells were transiently cotransfected with plasmid DNA encoding the Gq/11-coupled $a_{1B}$-adrenergic receptor (AR) or the $M_1$ AChR, the Gi-coupled $a_{2A}$-AR, or the Gs-coupled $D_{1A}$ dopamine receptor (0.1 mg DNA/well), plus either the Gaq(305–359) peptide minigene or empty vector (2.0 mg/well). Basal and agonist-stimulated IP or cAMP production was determined as described. Data are presented in arbitrary units such that one unit equals the basal level of IP or cAMP measured in unstimulated cells transfected with empty vector alone. Each panel represents mean ±SEM values for three separate experiments performed in triplicate. *, less than control; P<0.05.

FIG. 2. Myocardial expression of the GqI peptide. This is a representative immunoblot showing expression of the ~6 kDa GqI peptide which corresponds to amino acids 305–359 of the carboxyl-terminus of Gαq. 100 mg of myocardial extract from an NLC (Lane 1) and transgenic (Lane 2) heart was electrophoresed through a 10–20% Tricine SDS-PAGE mini-gel and transferred to nitrocellulose. A polyclonal antibody directed against the carboxyl-terminus region of Gαq was used for immunoblotting (DuPont NEN).

Figure 3A:
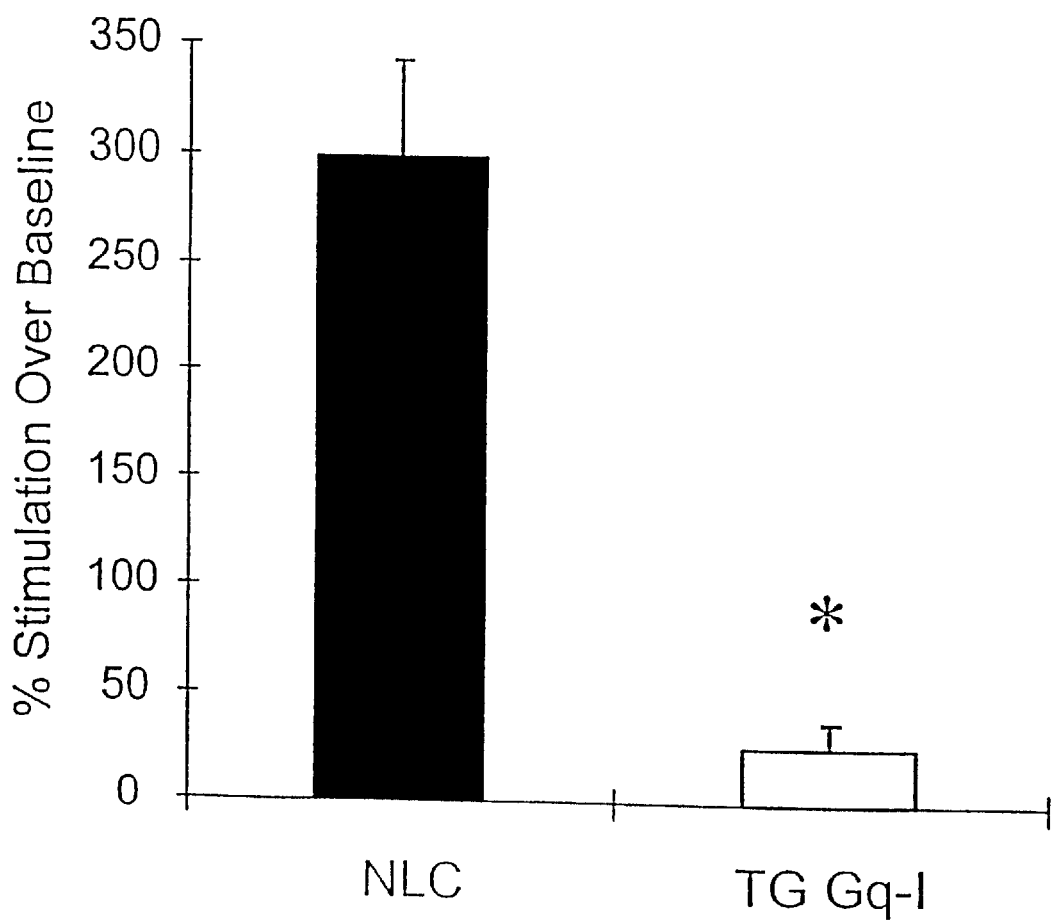

FIGS. 3A and B. Agonist-stimulated myocardial p42/44 MAP kinase activity. Left ventricular injections of the Gq-coupled receptor agonist angiotensin II (FIG. 3A) or endothelin I (FIG. 3B) were performed in NLC and TG GqI mice and myocardial MAP kinase activity was measured using myelin basic protein as a substrate for phosphorylation assays of immunoprecipitated p42/44 MAP kinase. Activity is expressed as the level of stimulation over saline-injected hearts used as baseline MAP kinase activity. The signals from the blots were counted on a Molecular Dynamics PhosphorImager. Data shown is the mean ±SEM for n=6 in each group. *$P<0.05$ versus NLC (student's t test).

Figure 4:
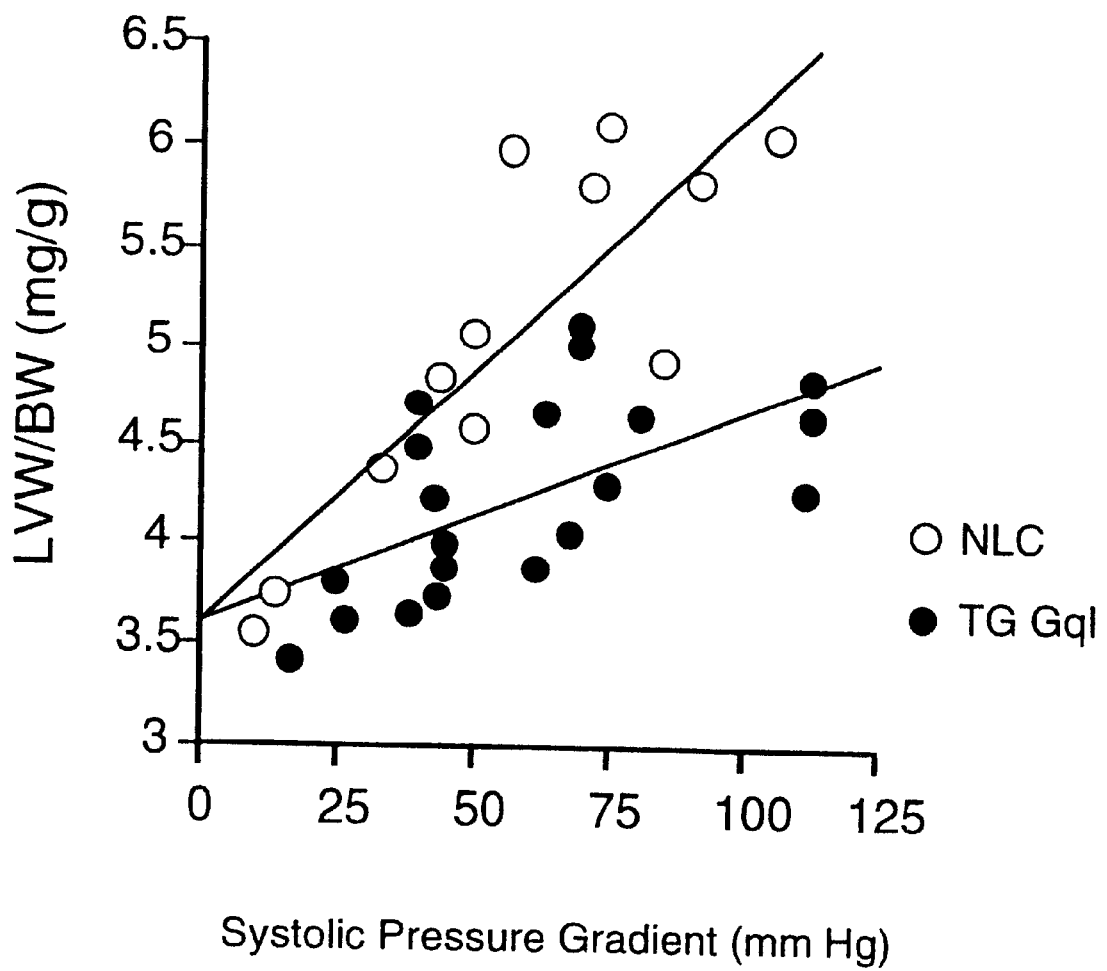

FIG. 4. Hypertrophic response to pressure overload. The index of left ventricular mass (LV/BW) is plotted against the systolic pressure gradient produced by transverse aortic constriction for each NLC (n=12) and TG GqI (n=20) animal. The slopes of the linear regressions for NLC (y=0.025x+3.61, r=0.85) and TG GqI (y=0.011x+3.61, r=0.60) animals were significantly different ($P<0.0005$, ANOVA).

Figure 5:
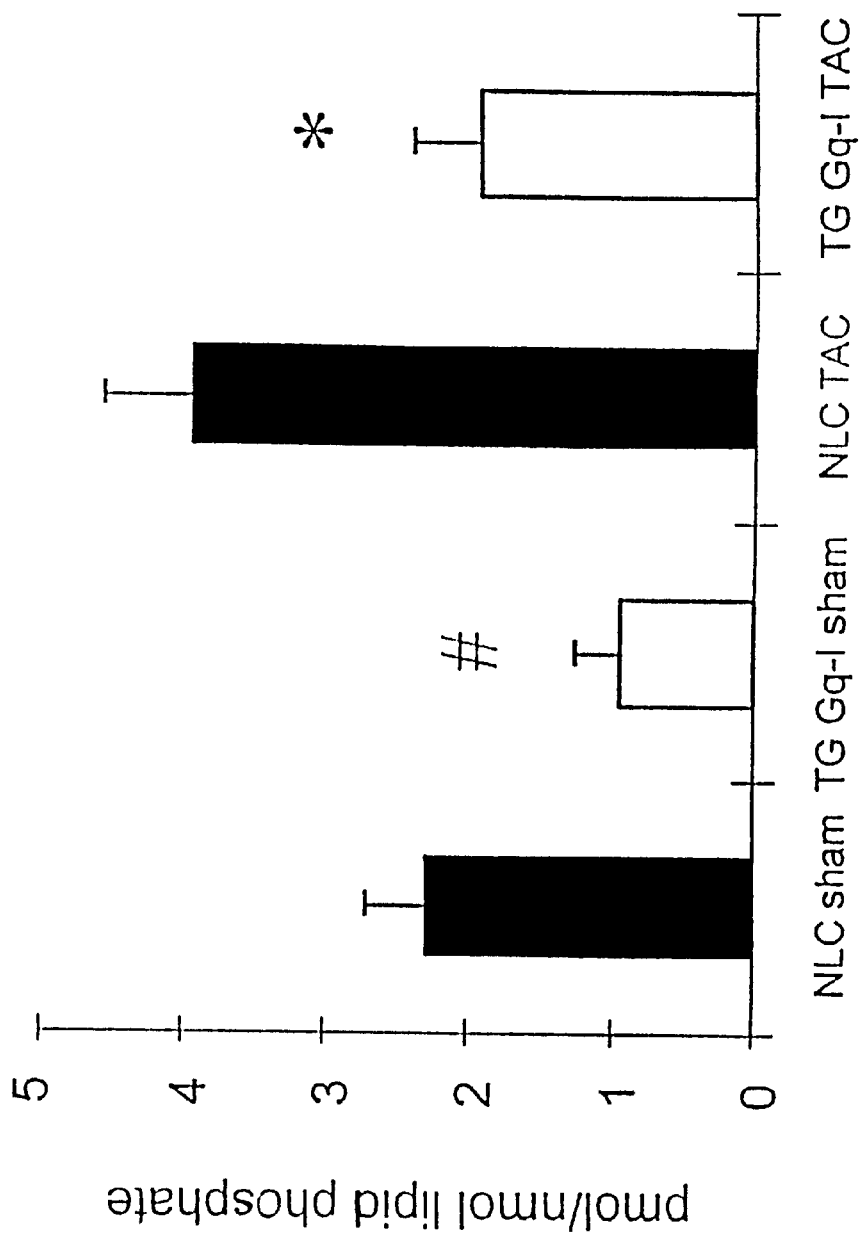

FIG. 5. Left ventricular diacylglycerol content for hearts undergoing sham-operation and transverse aortic constriction. Lipid extraction was performed from NLC (n=5) and TG GqI (n=5) left ventricles. Diacylglycerol content was quantified using 50 nmol of lipid phosphate as described. Data shown is mean ±SEM. #$P<0.05$ versus NLC sham and *$P<0.05$ versus NLC TAC (student's t test). Systolic pressure gradients produced by TAC were identical between groups.

Figure 6:
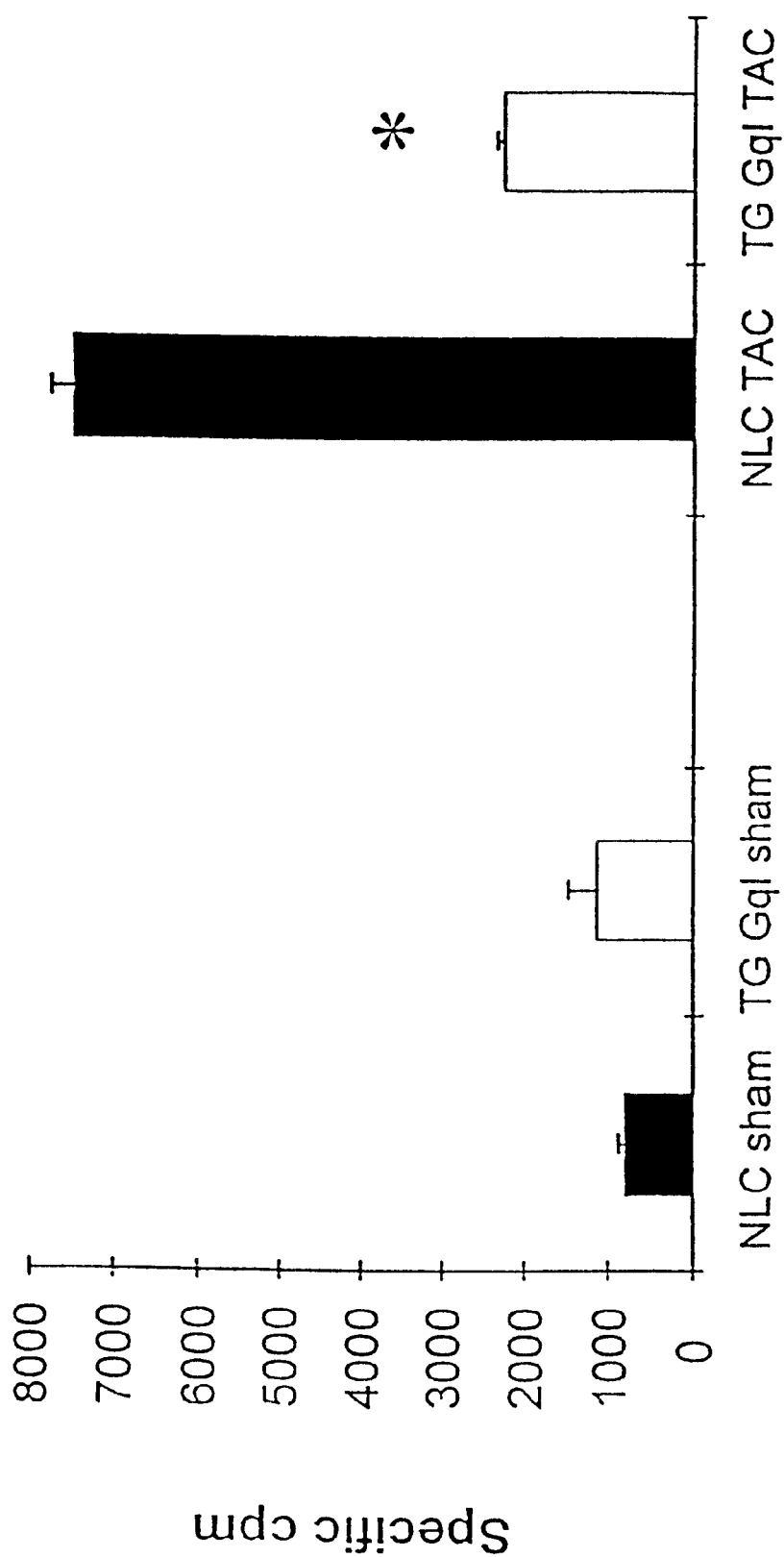

FIG. 6. Left ventricular ANF mRNA quantitation. Total RNA (15 mg) was isolated from the left ventricles of NLC and TG GqI hearts which underwent sham-operation or transverse aortic constriction. Northern blots were generated and probed with a mouse ANF cDNA. The blots were stripped and reprobed with rat GAPDH cDNA. The signals from the ANF blots were counted on a Molecular Dynamics PhosphorImager and normalized to the GAPDH signal as described. Data shown is the mean ±SEM for n=5 in each group. *$P<0.05$ versus NLC TAC (student's t test).

DETAILED DESCRIPTION OF THE INVENTION

The present invention results from studies demonstrating that Gq-coupled signal transduction plays an obligatory role in the pathogenesis of ventricular hypertrophy. These studies were carried out using transgenic mice with targeted myocardial expression of the carboxy-terminal 55 amino acids of the α-subunit of Gq which inhibits Gq-coupled signaling. Inhibition of Gq-coupled signaling in these animals led to a decline in ventricular atrial natriuretic factor (ANF) gene expression (a molecular marker of hypertrophy) and a reduction in myocardial diacylglycerol (DAG) levels, a product of Gq activation.

In one embodiment, the present invention relates to a method of inhibiting Gq-mediated receptor signaling in a mammal in need of such inhibition. The method comprises administering to the mammal an agent that inhibits Gq-mediated receptor signaling, which agent is administered in an amount, and under conditions such that, signal inhibition is effected.

This method of the invention is applicable to mammals, eg humans, suffering a cardiovascular disease or disorder associated with myocardial hypertrophy or vascular smooth muscle proliferation and/or migration. The method can be used to improve survival in cardiac disease patients (for example, in patients undergoing myocardial hypertrophy by preventing transition to failure), to treat hypertension, to treat atherosclerosis, to inhibit restenosis, for example, following angioplasty, and to prevent vein graft failure, for example, due to intimal hyperplasia.

Agents suitable for use in the present method include both proteinaceous and non-proteinaceous compounds. As shown in the Examples that follow, specific inhibition of Gq-mediated signaling can be effected using a peptide corresponding to a carboxy terminal portion of the alpha subunit of Gq (Gαq), eg amino acids 305–359. Compounds suitable for use in the method of the invention, eg small non-proteinaceous molecules, can block activation of G protein by binding Gq-coupled receptor.

Administration of the Gq-mediated signaling inhibitors of the invention can be effected using any of a variety of approaches, the preferred approach varying with the inhibitor, the patient and the effect sought. In the case of proteinaceous inhibitors, administration can be accomplished using gene therapy regimens. Such regimens utilize a nucleic acid (eg DNA) sequence encoding a protein/peptide inhibitor of Gq-mediated signaling. The encoding sequence can be present in a construct which, when introduced into target cells, results in expression of the nucleic acid sequence and production of the inhibitor. Target cells include myocardial cells and vascular smooth muscle cells. Delivery of the inhibitor encoding sequence can be effected using any of a variety of methodologies. The encoding sequence can be delivered directly, ie via a catheter, to the target site, for example, when inhibition of restenosis or prevention of vein graft failure is the goal. Where direct (ie local) delivery is not possible or not preferred, targeted expression can be effected by utilizing a tissue specific promoter. Examples of such promoters include myocyte specific promoters such as the α myosin heavy chain gene promoter. When direct delivery is possible, a constitutive, promoter such as the CMV, can be used (eg for vasculature). The actin promoter can also be used, as can the myosin light chain promoter. Other delivery methodologies include transfection with a viral vector and fusion with a lipid. Selection of which technique to use depends upon the particular situation.

Replication-defective retroviral vectors harboring the therapeutic polynucleotide sequence as part of the retroviral genome can be used to effect gene transfer; adenoviral vectors can also be used. Alternatively, adenoassociated viruses, which integrate, can be used, as can other viral systems depending on the target site. (See Peppel et al, Trends Cardiovas. Med. 7, July (1997)). Another gene transfer method suitable for use in humans is physical transfer of DNA (or RNA) in liposomes directly into target cells in situ. Liposome-mediated DNA (or RNA) transfer has been described by various investigators. (See generally Nabel et al, Cardiovas. Res. 28:445 (1994)).

Essentially, any suitable DNA delivery method can be used in the context of the present invention, including direct physical application of naked DNA comprising the expression construct/transgene to the target cell population.

Nucleic acid-containing compositions of the invention can be stored and administered in a sterile physiologically acceptable carrier, where the nucleic acid is dispersed in conjunction with any agents which aid in the introduction of the nucleic acid into cells. The concentration of the nucleic acid is sufficient to provide a therapeutic dose, which will depend on the efficiency of transport into the cells. Actual delivery of the gene sequence can be carried out by a variety of techniques including direct injection, intravenous injection and other physical methods. Administration can be by syringe needle, catheter, etc, as a bolus, a plurality of doses or extended infusion, etc.

The compositions containing the present inhibitor encoding sequence can be administered for prophylactic and/or therapeutic treatments. In therapeutic application, compositions are administered to a patient already affected by the particular cardiac or vascular disease or disorder, in an amount sufficient to inhibit Gq-mediated signaling. Amounts effective for this use will depend upon the severity of the condition, the general state of the patient, the activity of the encoded peptide and the route of administration.

In addition to the above-described approaches, cells transformed in vitro with inhibitor-encoding sequences can be implanted at the target site.

In a further embodiment, the present invention relates to a in vivo method of selecting peptides for their ability to inhibit Gq-coupled receptor signaling. This embodiment utilizes a transgenic animal (eg, a rodent, advantageously, a mouse) the cells of which contain a transgene encoding a peptide to be tested. The encoding sequence can be present in operable linkage with a tissue-specific promoter, for example, a myocyte-specific promoter such as the α-myosin heavy chain gene promoter, or a constitutive promoter, for example, where direct delivery is effected. Such animals can be generated using any of a variety of techniques, including that described in the Examples that follow. (See Koch et al, Circulation Res. 78:511 (1996)). In accordance with this method, the transgenic animal is treated with an agonist for endogenous Gq-coupled receptors (eg angiotensin II and endothelin) and the functional activity of the test peptide on Gq signaling (eg myocardial Gq signaling) determined. The activity of the test peptide can be determined by monitoring the level of an indicator of hypertrophy, such as ANF expression, or DAG content or the level of an enzyme such as the p42/p44 mitogen-activated protein (MAP) kinase. Attenuation of indicator (eg MAP kinase) activity in an agonist-treated transgenic animal, relative to an agonist-treated control (non-transgenic) littermate, is indicative of a peptide that inhibits Gq-coupled signaling.

Transgenic animals as described above can also be subjected to pressure overload by mechanical (eg surgical) techniques, including by transverse aortic constriction (TAC). An attenuation of hypertrophy in the transgenic animal in response to pressure overload so produced, relative to a control non-transgenic animal, is also indicative of a peptide that inhibits myocardial Gq-mediated signaling.

Agents (proteinaceous and non-proteinaceous) can also be screened for usefulness in the treatment method of the invention using non-transgenic animals subjected to pressure overload (eg surgically, as described above). (See Choi et al, J. Biol. Chem. 272:17223 (1997).) Alternatively, a cell system or vein graft model can be used (see below and Luttrell et al, Science 259:1453 (1993)).

The invention includes within its scope not only the above-screening methods but also the transgenic animals utilized therein and constructs suitable for use in the generation of such animals (eg constructs comprising a tissue (eg myocardium) specific promoter operably linked to a nucleic acid sequence encoding a specific Gq-mediated signaling inhibitor—such as the peptide described in the Examples below).

Certain aspects of the invention are described in greater detail in the non-limiting Examples that follow.

EXAMPLES

The following experimental details are referenced in the specific Examples that follow.
DNA Constructs:

The cDNAs for the hamster $a_{1B}$-adrenergic receptor (AR) and human $a_{2A}$-AR were cloned. The cDNAs for the human $M_1$, AChR, the human $D_{1A}$ dopamine receptor and Gaq were obtained from other investigators. For transient cellular expression, cDNAs were subcloned into the eukaryotic expression vector pRK5. All minigene constructs contained an EcoR1 restriction site at the 5'-end for subcloning, followed by the ribosome binding consensus sequence 5'-GCCGCCACCATG-3' (SEQ ID NO:1). The specific cDNA fragments that encode the desired peptide were next, followed by a TAA stop codon, a Bcl1 restriction site, and the 3'-untranslated region of the human b-globin gene which was incorporated to enhance the stability of the messenger RNA. At the 3'-end of the minigene, an Sma1 restriction site was engineered for subcloning. The peptide-encoding cDNA fragments were obtained using the polymerase chain reaction with specific oligonucleotide primers to amplify the region of interest. Following the initiator methionine, each minigene construct contained glycine as the second amino acid in order for the Gly codon (GGA) to protect the ribosome binding site during translation and to protect the nascent polypeptide against proteolytic degradation. All restriction sites and signaling sequences, and the splice site between the peptide coding region and the b-globin gene 3'-UTR were introduced during PCR amplification. The amplified EcoR1/Sma1 minigene cassettes were subcloned into the pRK5 vector for eukaryotic cell expression. Minigene sequences were confirmed by dideoxynucleotide sequencing.

Cell Culture and Transfection:

Transient transfection studies were performed using COS-7 cells. COS-7 cells were maintained in Dulbecco's modified Eagle's medium (DMEM) supplemented with 10% fetal bovine serum (FBS) and 100 mg/ml gentamicin at 37° C. in a humidified, 5% $CO_2$ atmosphere. Cells were seeded in 6 well tissue culture plates ($1\times10^5$ cells/well) the day prior to transfection, and transfected by the DEAE-dextran method using a total of 1–2 mg DNA/well. Assays were performed 48 h after transfection. In all transfections, the minigene-containing plasmid DNA was included at 10-fold excess over the receptor construct in order to assure that cells in the transfected population that carry the receptor also carry the minigene product. Empty pRK5 vector was added to control transfections as needed to keep the total mass of DNA added per well constant within an experiment.

Documentation of Minigene Expression:

Expression of the intact Gaq-subunit and minigene products encompassing the Gaq carboxy-terminus were determined by protein immunoblotting. Transfected cells were harvested and lysed in RIPA buffer (50 mM Tris-HCl, pH 7.5, 150 mM NaCl, 1% Nonidet NP-40, 0.25% Deoxycholate). After centrifugation, cytosolic extracts (10–20 mg of protein) were denatured by boiling in Laemmli sample buffer, resolved on 10–20% gradient tricine SDS-polyacrylamide gels (Novex), transferred to nitrocellulose and probed using rabbit anti-Gaq/Ga11 antiserum raised to the Ga-subunit carboxy-terminus (Dupont NEN) with $^{125}$I-Protein A (Amersham) for detection. Protein bands were visualized by autoradiography.

Ligand Binding:

Receptor expression was quantitated by saturation binding. For saturation binding analysis, crude plasma membranes prepared from transfected COS-7 cells lysed in 5 mM Tris-HCl (pH 7.4), 5 mM EDTA were resuspended at an appropriate dilution in 50 mM Tris-HCl (pH 7.4), 150 mM NaCl, 5 mM EDTA and incubated with a saturating concentration of radioligand for 1 h at 25° C. with or without an excess of unlabelled ligand to determine nonspecific binding. Following incubation, bound and unbound radioligand were separated by filtration over glass fiber filters. Expression of $a_{1B}$-ARs was measured as the binding of 1 nM 2-[b-(4-hydroxy-3-[$^{125}$I]iodophenyl)ethylaminomethyl] tetralone ([$^{125}$I]-HEAT) (Dupont NEN) using 1 mM prazocin (Sigma) to determine nonspecific binding. Expression of $a_{2A}$-AR was measured as the binding of 1 nM [$^3$H]-rauwolscine (Dupont NEN) using 1 mM yohimbine (Sigma)

to determine nonspecific binding. Expression of $M_1$ AChR was measured as the binding of 1 nM L-[benzilic-4,4'-$^3$H (N)]-quinuclidinyl benzilate ([$^3$H]-QNB) (Dupont NEN) using 10 mM atropine (Sigma) to determine nonspecific binding. Binding data were normalized per mg of membrane protein. Nonspecific ligand binding was typically less than 10% of the total.

Inositol Phosphate and cAMP Production:

For measurement of total inositol phosphates (IPs), transfected COS-7 cells were labelled for 18–24 h with 2 mCi/ml [$^3$H]-myo-inositol (Dupont NEN) in culture medium supplemented with 3% FBS. After labelling, cells were washed for 20 min at 37° C. with calcium-free Dulbecco's phosphate buffered saline (DPBS), preincubated for 20 min in DPBS supplemented with 20 mM LiCl and 1 mM $CaCl_2$ and stimulated for 45 min with or without agonist [10 mM epinephrine (Sigma) for the $a_{1B}$AR, 10 mM UK-14304 (Pfeizer) for the $a_{2A}$ AR, 100 mM carbachol (Sigma) for the $M_1$ AChR and 10 mM fenoldopam (SmithKline and Beecham) for the $D_{1A}$ DR]. Following stimulation, IPs were extracted in 0.4 M perchloric acid (1 ml/well), 0.8 ml of each sample was neutralized with 0.4 ml of 0.72 M KOH, 0.6 M KHCO3 and 1.0 ml of the neutralized supernatant analyzed for total IPs. Total IPs were separated on Dowex AG1-X8 columns, eluted with 1 M ammonium formate, 0.1 M formic acid and quantitated by liquid scintillation counting.

For measurement of intracellular cAMP, transfected COS-7 cells were labelled for 18–24 h with 2 mCi/ml [$^3$H]-adenine (Dupont NEN) in culture medium supplemented with 3% FBS. After labelling, cells were preincubated for 15 min at 37° C. in 1 ml of Hank's balanced salt solution supplemented with 10 mM HEPES (pH 7.4) and 1 mM isobutylmethylxanthine, and stimulated for 20 min with or without agonist. Reactions were terminated by aspiration of the medium and addition of 1 ml of stop solution (2.5% perchloric acid, 100 mM cAMP, 10,000 cpm/ml $^{14}$C-cAMP). Samples were neutralized with 0.1 ml of 4.2 M KOH, and cAMP in 0.85 ml aliquots was separated by sequential chromatography on Dowex AGW50-X4 and aluminum oxide columns using the trace amounts of [$^{14}$C]-cAMP to assess column recovery.

Generation of Transgenic Mice:

A Sal I-Sac I, 5.5 kilobase fragment, containing the murine a-MHC promoter (Subramanian et al, J. Biol. Chem. 266:24613 (1991) was ligated into a previously described plasmid containing the SV-40 intron poly(A) signal (Milano et al, Proc. Natl. Acad. Sci. USA 91:10109 (1994)) to generate the new plasmid, pGEM-a-MHC-SV-40 (see Milano et al, Science 264:582 (1994)). A 300 base pair fragment, containing the coding sequence for the carboxy-terminal amino acids 305–359 of murine Gaq (GqI) was ligated into pGEM-a-MHC-SV-40 to generate pGEM-a-MHC-GqI-SV-40. The transgene was then linearized and purified before pronuclear injections done by the Duke Comprehensive Cancer Center Transgenic Facility (Milano et al, Proc. Natl. Acad. Sci. USA 91:10109 (1994)). Litter sizes and postnatal development were indistinguishable from nontransgenic littermate controls. Offspring were screened by Southern blot analysis with a probe to the SV-40 sequences. Second generation adult animals, 2–4 months of age, were used for all studies. Institutional Review Board approval for all mouse experiments was obtained from the University of California at San Diego and from Duke University Medical Center.

Protein Immunoblotting:

Transgenic and control mouse hearts were each homogenized in 2 ml of RIPA buffer and underwent centrifugation at 40,000 g for 30 minutes. The supernatant myocardial extracts were concentrated using a Centricon 3 microconcentrator (Amicon). Protein concentrations were determined by the BCA protein assay. 150 mg of transgenic and control myocardial extract were electrophoresed through 10–20% Tricine-SDS polyacrylamide gels (Novex) and transferred to nitrocellulose. The membrane was blocked in 5% nonfat dried milk in 0.1% Tween 20/phosphate buffered saline (PBS-T) for 1 hour at RT. The membrane was then washed for 15 minutes in PBS-T and incubated with a polyclonal anti-Gaq/$Ga_{11}$ antibody (DuPont NEN) at a 1:1,000 dilution in PBS-T overnight at 4° C. The membrane was again washed in PBS-T as above and incubated with an anti-rabbit-HRP-linked secondary antibody (Amersham) diluted 1:3,000 in PBS-T for 1 hour at RT. The blot was washed once again as above and detection was performed by ECL (Amersham).

Mitogen Activated Protein Kinase Activity:

Mice were anesthetized with with a mixture of ketamine (100 mg/kg, i.p.) and xylazine (2.5 mg/kg, i.p.). The thorax was entered through a left anterior thoracotomy and a direct left ventricular intracavitary injection of 100 ml of either phosphate-buffered saline (PBS), 100 mM angiotensin II, or 100 mM endothelin I was administered. Ninety seconds after injection, while still in sinus rhythm, the heart was excised and snap frozen in liquid $N_2$. The hearts were homogenized in 2 ml of RIPA buffer and then centrifuged at 40,000 g for 30 minutes. The protein content of the supernatant fraction was determined by the BCA protein assay. Using 30 ml of a 1:10 dilution of anti-ERK 2 antibody (Santa Cruz) in Protein A-agarose, 10 mg of myocardial extract in 1 ml total volume of RIPA was immunoprecipitated at 4° C. for 2 hours. The samples were then centrifuged at 18,000 g for 10 minutes and the pellets washed twice with 1 ml of RIPA and twice with 1 ml of kinase buffer (20 mM Hepes, pH 7.0/10 mM $MgCl_2$, 1 mM DTT). The pellets were resuspended in 40 ml of reaction buffer (kinase buffer with 0.25 mg/ml myelin basic protein (MBP), 20 mM ATP, and 20 mCi/ml [$^{32}$P]g-ATP and icubated at RT for 30 minutes. The reactions were quenched with 40 ml of 2× Laemmli buffer. 30 ml of each reaction was electrophoresed through a 4–20% Tris-Glycine gradient gel (Novex). The gels were dried and exposed to x-ray film overnight. The MBP band was quantitated using a PhosphorImager (Molecular Dynamics).

Adenylyl Cyclase Activity:

Crude myocardial membranes were prepared by homogenizing hearts in 5 mM Tris-HCl, pH 7.4/5 mM EDTA followed by centrifugation at 500 g for 15 minutes. The supernatants were then filtered through 2 layers of cheesecloth and centifugation was performed at 40,000 g for 15 minutes. The membrane pellets were resuspended in 1 ml of 75 mM Tris-HCl/12.5 mM $MgCl_2$/2 mM EDTA (pH 7.4). Membranes (20–30 mg of protein) were incubated for 15 minutes at 37° C. with [$^{32}$P]a-ATP under basal conditions or in the presence of either progressive doses of isoproterenol or 10 mM NaF (Milano et al, Science 264:582 (1994)). Cyclic AMP was quantitated by standard methods described previouly (Salomon et al. Anal. Biochem. 58:541 (1974)).

Chronic Transverse Aortic Constriction:

Mice were anesthetized with a mixture of ketamine (100 mg/kg, i.p.) and xylazine (2.5 mg/kg, i.p.). Using microsurgical procedures as previously described (Rockman et al, Proc. Natl. Acad. Sci. USA 88:8277 (1991), Choi et al, J. Biol. Chem. 272:17223 (1997)), under a dissecting microscope (Scope Instruments, San Diego, Calif.) animals were placed in a supine position and a midline cervical incision made to expose the trachea and carotid arteries. Endotracheal intubation was performed using a blunt 20 gauge needle which was then connected to a volume-cycled rodent ventilator (Harvard Apparatus, Model 683) with a tidal volume of 0.2 ml and respiratory rate of 104/minute. The thoracic cavity was entered in the second intercostal space, and the transverse aorta between the right (proximal) and left (distal) carotid arteries was isolated. Transverse aortic constriction (TAC) was performed by placing a 7-0 nylon suture ligature against a 27 gauge needle, the latter being promptly removed to yield a reproducible transverse aortic constriction of 65–70% (Rockman et al. Proc. Natl. Acad. Sci. USA 88:8277 (1991)). Following aortic constriction the chest was closed, the pneumothorax evacuated with a modified chest tube, and the mice extubated and allowed to recover from anesthesia. Sham-operated animals underwent the same operation except for aortic constriction. After 7 days of aortic constriction, mice were anesthetized as above. A midline incision was made to expose both right and left carotid arteries which were then cannulated using flame stretched PE 50 tubing connected to modified P50 Statham transducers. Simultaneous measurement of right and left carotid artery pressures was recorded after bilateral vagotomy. Experiments were then terminated with an overdose of pentobarbital. Hearts were excised, chambers dissected free and weighed, then snap frozen in liquid $N_2$. To eliminate potential bias from post-operative weight loss in the aortic constricted animals, the largest of the pre- and post-operative body weights were used to calculate left ventricle to body weight ratios.

Diacylglycerol (DAG) Quantitation:

Lipid fractions were extracted from 50 mg of homogenized myocardial tissue as previously described (Milano et al, Proc. Natl. Acad. Sci. USA 91:10109 (1994)). Aliquots of lipid and DAG standards were dried under vacuum, resuspended in detergent micelles, and then completely phosphorylated using Escherichia coli DAG kinase (Amersham) and [$^{32}$P]g-ATP. $^{32}$P-labeled phosphatidic acid (phosphorylated DAG) was isolated by silica gel thin-layer chromatography and quantitated with a PhosphorImager (Molecular Dynamics). DAG content was normalized to tissue phospholipid and the final DAG content was expressed as pmol of DAG per nmol of lipid phosphate as described previously (Milano et al, Proc. Natl. Acad. Sci. USA 91:10109 (1994).).

Ventricular ANF mRNA:

Ventricular tissue was separated from the atria under a dissecting microscope. Total RNA was extracted using RNAzol (Biotecx, Houston, Tex.), a single-step guanididium-based isolation procedure (Chomczynski et al. Anal. Biochem. 162:156 (1987). Total RNA was then fractionated on a 1% agarose-formaldehyde gel and transferred to nitrocellulose as previously described (Milano et al, Proc. Natl. Acad. Sci. USA 91:10109 (1994)). Blots were prehybridized in a 50% formamide solution for 4 hours at 42° C. and then hybridized overnight with a random primer, radiolabeled ANF cDNA probe (Milano et al, Proc. Natl. Acad. Sci. USA 91:10109 (1994)). Blots were washed three times in 0.2x SSC at 65° C. for 30 minutes before exposure to x-ray film. All blots were then stripped in water at 95–100° C. for 15 minutes and reprobed with a rat glyceraldehyde-3-phosphate dehydrogenase (GAPDH) cDNA probe. The ANF and GAPDH bands were quantitated with a PhosphorImager (Molecular Dynamics) and the ANF:GAPDH signal intensity ratio was determined.

Example 1

In Vitro Receptor Uncoupling by a Gaq Carboxy-terminal Peptide

Figure 1A:
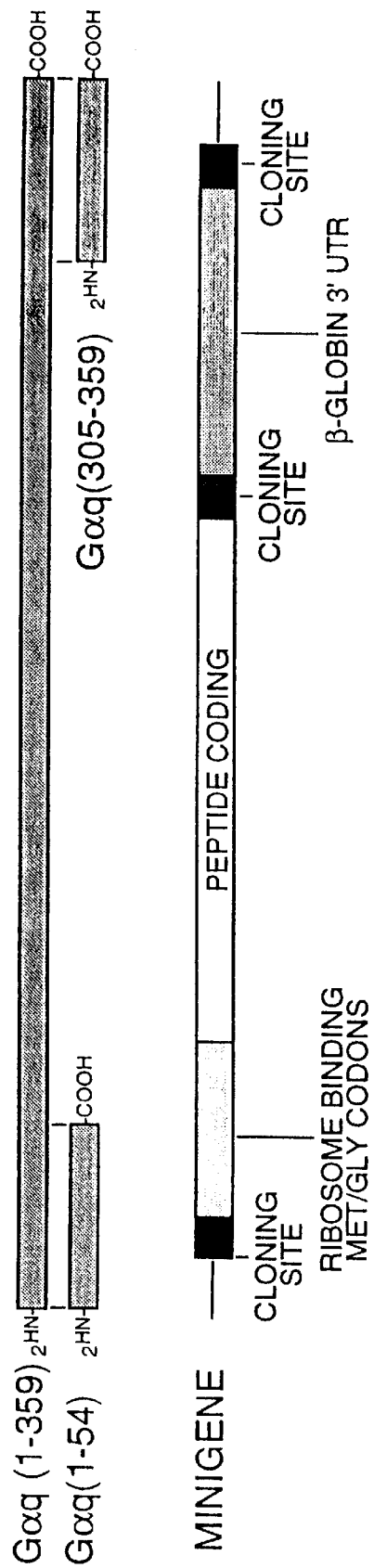
Figure 1B:
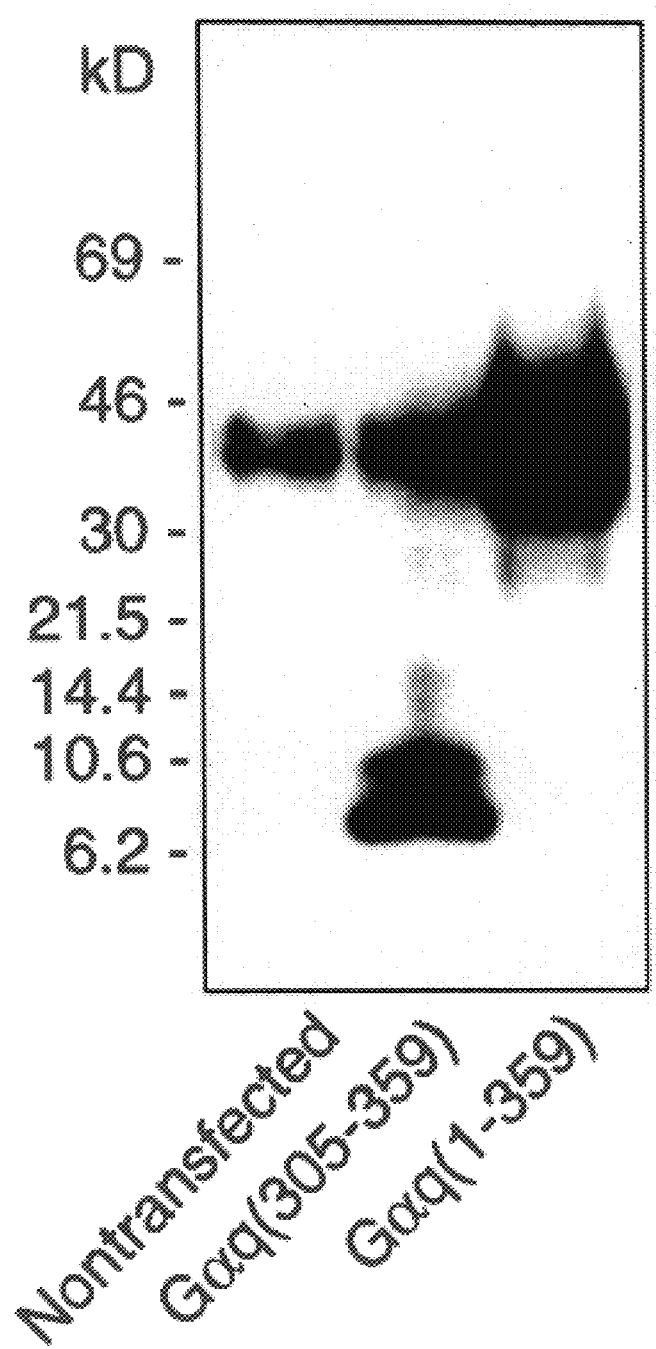
Figures 1, 1C:
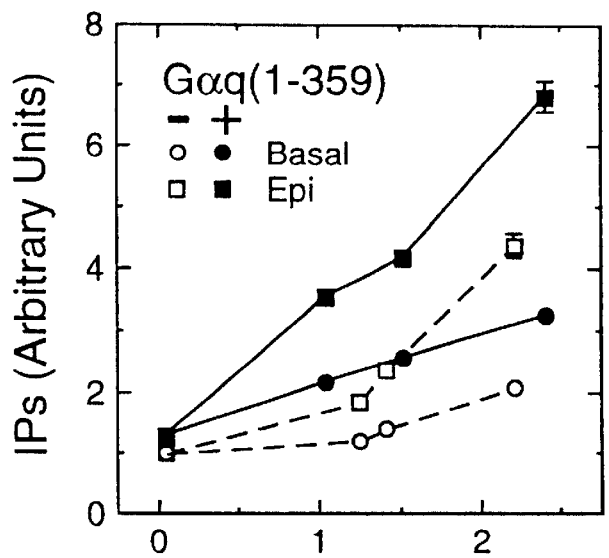

Two Gaq minigene constructs were created which correspond to the carboxy-terminal peptide sequence Gaq (305–359), and the amino-terminal peptide sequence Gaq (1–54) (FIG. 1A). COS-7 cells were transiently transfected with plasmid DNA encoding the Gaq minigenes and the expression of the Gaq-carboxyl-terminal epitope in whole cell detergent lysates was demonstrated by protein immunoblotting (FIG. 1B). Coexpression of $a_{1B}$-adrenergic receptors (ARs) with the intact Gaq subunit led to enhancement of epinephrine-stimulated PI hydrolysis compared to cells expressing equal numbers of receptors alone. In contrast, coexpression of Gaq (305–359) resulted in a significant (47.8±4.4%) inhibition of maximal $a_{1B}$-AR-mediated PI hydrolysis (FIG. 1C). Coexpression of a 54 amino acid peptide corresponding to the Gaq amino-terminus (Gaq 1–54) had no effect, supporting the hypothesis that the carboxy-terminal region of the Ga subunit contributes to the receptor-G protein interface in an intact cell system. The inhibition produced by the Gaq (305–359) peptide was specific for Gq-coupled receptors as neither $a_{2A}$-AR-mediated IP production (Gi-coupled) nor dopamine $D_{1A}$ receptor-mediated cAMP production (Gs-coupled) were inhibited (FIG. 1D).

Example 2

In Vivo Receptor Uncoupling by a Gaq Carboxy-terminal Peptide

Figures 1, 1C, 2:
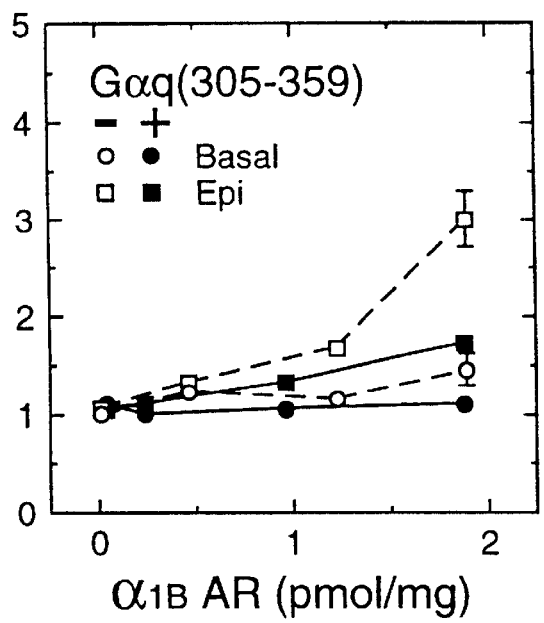
Figures 1, 1C, 2, 3:
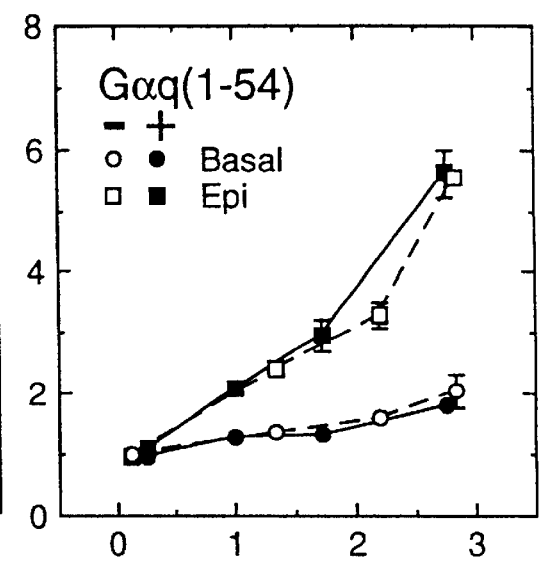
Figure 2:
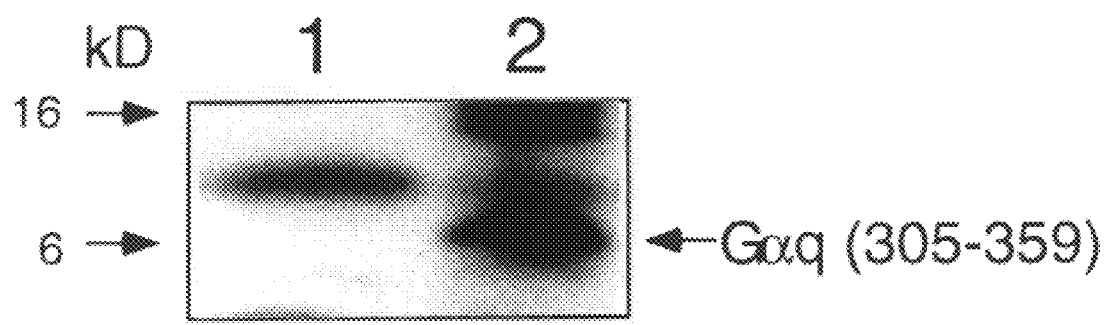

In order to study the effects of this peptide on Gq-mediated signaling pathways in vivo, transgenic mice were created with cardiac-specific expression of Gaq (305–359). This Gq inhibitor transgene (GqI) was targeted to the myocardium by linking it with the murine a-myosin heavy chain (a-MyHC) promoter which we have successfully used to target other G protein-coupled signaling components (Koch et al, Cir. Res. 78:51 (1996)). Five founder lines that transmitted the transgene were established and named TG GqI-8, TG GqI-10, TG GqI-11, TG GqI-26, and TG GqI-38. The TG GqI-10 line had the greatest transgene expression as shown by Northern analysis and heterozygous (+/−) animals of this line were subsequently used in all further studies. At ten weeks of age, GqI peptide expression was documented by protein immunoblotting in the TG GqI-10 line (FIG. 2). These transgenic mice were normal in size and appearance compared to their nontransgenic littermate controls (NLC) from birth until the adult age (10 weeks) at which they were studied. The litter sizes also were unremarkable.

Figure 3B:
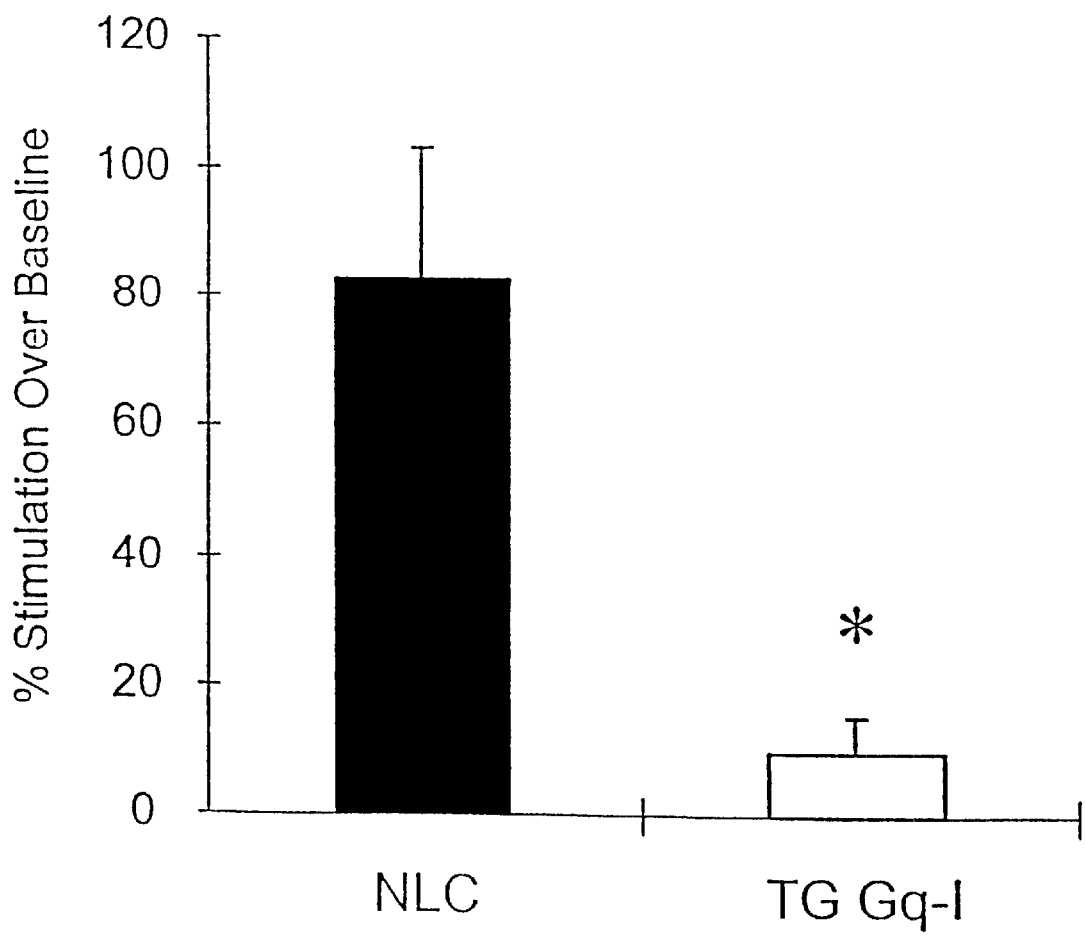

To examine the functional activity of the Gaq inhibitor peptide on myocardial Gq signaling in vivo, we studied p42/p44 mitogen-activated protein (MAP) kinase activity in response to two agonists for endogenous myocardial Gq-coupled receptors, angiotensin II (Ang II) and endothelin I. In anesthetized transgenic and NLC mice, we directly injected 100 ml of the appropriate agonist into the left ventricular (LV) chamber via a left thoracotomy. Ninety seconds later, the hearts, still in sinus rhythm, were excised and snap-frozen in liquid $N_2$ for analysis. Agonist-mediated LV MAP kinase activity was compared to hearts injected with saline. In NLC hearts, Ang II provoked an approximate 4-fold increase in MAP kinase activity. In the TG GqI mice, stimulation resulted in only a 1.3-fold increase in MAP kinase activity (FIG. 3A). This represents an ~80% decrease in this Gq-mediated response. Endothelin I-stimulated myocardial MAP kinase activity in TG GqI mice was comparably reduced after cardiac injection of endothelin I (FIG. 3B). Similar results were obtained using the $a_1$-AR agonist phenylephrine. Mice of a second line (TG GqI-8) were also studied and MAP kinase activity in response to Ang II was similarly attenuated. There was no significant difference in basal MAP kinase activity between TG-GqI and NLC myocardial extracts. These data indicate that myocardial GqI expression effectively inhibits signal transduction via at least three distinct Gq-coupled receptors in the intact, beating heart.

To confirm that this in vivo attenuation of agonist-stimulated signaling is specific for Gq-coupled receptors, basal and agonist-stimulated myocardial sarcolemmal membrane adenylyl cyclase activity was measured in membranes derived from TG GqI and NLC mice. In the heart, adenylyl cyclase activity is regulated primarily by b-ARs coupled to the G protein, Gs. As shown in Table 1 neither basal nor b-agonist (isoproterenol) stimulated adenylyl cyclase activity was different for the TG GqI versus NLC myocardial membrane extracts. Consistent with the findings in transiently transfected COS-7 cells, these data indicate that the GqI peptide is specific for Gq-coupled receptor signaling in vivo.

TABLE 1

Myocardial Sarcolemmal Membrane Adenylyl Cyclase Activity

| Hearts | Basal | ISO ($10^{-8}$ M) | ISO ($10^{-6}$ M) | ISO ($10^{-4}$ M) |
|---|---|---|---|---|
| Control (NLC) | 44.2 ± 9.7 | 46.7 ± 9.2 | 59.9 ± 7.8 | 62.9 ± 7.0 |
| TG GqI | 41.3 ± 5.2 | 45.0 ± 5.8 | 61.0 ± 8.8 | 59.8 ± 7.2 |

Activity presented as pmol cAMP per minute per mg protein. ISO, Isoproterenol. Data expressed as Mean ± SEM. N = 5 in each group. P > 0.05 for all conditions between Control and TG GqI (t test).

Example 3

Myocardial Expression of the GqI Peptide Attenuates Pressure Overload Hypertrophy While many of the features of myocardial hypertrophy can be reproduced in vitro, the precise molecular signaling pathways regulating these hypertrophic responses in vivo have not yet been fully elucidated. To directly assess the in vivo physiological significance of Gq-coupled receptor signaling in the development of pressure overload hypertrophy, TG GqI and NLC mice were subjected to pressure overload by surgical transverse aortic constriction (TAC). In this model, a significant and reproducible systolic pressure gradient is created by TAC as measured between the carotid arteries. Significant LV hypertrophy can be seen 7 days after surgery (Choi et al, J. Biol. Chem. 272:17223 (1997)) and Rockman et al. Proc. Natl. Acad. Sci. (1991)) using LV weight to body weight (BW) ratio as an index of myocardial mass. As shown in Table 2, there was no difference in the LV/BW between sham-operated TG GqI and NLC mice. In the TAC group, the NLC LV/BW increased by 36% over sham. In contrast, the TG GqI mice 7 days after TAC had only a 14% increase in LV/BW over sham-operated TG GqI mice. This difference in myocardial mass was highly significant (P<0.01). Importantly, the mean systolic pressure gradient created by TAC, an index of the load placed on the ventricle, was not different between the two groups: 66.4±7.4 mmHg for NLC TAC and 62.3±6.8 mmHg for TG GqI TAC (P=NS). FIG. 4 demonstrates that across a wide range of systolic pressure gradients measured, the LV/BW is significantly lower for the TG GqI mice compared to NLC. Thus, in vivo inhibition of myocardial Gq-mediated signaling leads to significant attenuation of LV hypertrophy in response to pressure overload indicating that Gq-coupled receptor agonists play a critical role in triggering this response following the mechanical stimulus of hemodynamic stress.

Example 4

Gq-coupled Receptor Signaling Characteristics of Pressure Overload Hypertrophy

To further delineate the role of Gq inhibition on the hypertrophic response, biochemical sequelae occurring in response to pressure overload were studied in the TG GqI and NLC mice after TAC. Classical Gq-coupled receptor stimulation leads to activation of phospholipase C and the generation of the second messengers $IP_3$ and DAG. As a direct measurement of Gq activation, LV DAG content was measured both under basal conditions and after TAC. As shown in FIG. 5, basal LV DAG content, as assessed in sham-operated hearts, was significantly depressed in the TG GqI mice as compared to NLC animals. This finding indicates that basal Gq-signaling is decreased in the transgenic hearts and represents further evidence for the in vivo Gq-inhibitory properties of the GqI transgene. After TAC, the LV DAG content in the NLC group increased by 73% indicating a significant enhancement of Gq-coupled signaling in response to pressure overload (FIG. 5). These data directly demonstrate increased myocardial Gq signal transduction in response to pressure overload in the intact mouse. In the TG GqI group after TAC, LV DAG content increased only to a level slightly higher than that seen in the sham-operated NLC mice and significantly lower than TAC-treated NLC mice (FIG. 5). Since the depression of basal DAG levels in TG GqI mice did not affect LV/BW ratios in the absence of pressure overload, it is possible that Gq-mediated signals do not influence the normal growth of adult myocytes. In contrast, the attenuation of Gq-coupled signaling in the TG GqI mice, as indicated by the significantly lower DAG in response to pressure overload, is associated with a corresponding reduction of LV hypertrophy.

In previously reported in vivo models, myocardial hypertrophy associated with enhanced Gq signaling is accompanied by reactivation of ventricular embryonic genes including ANF, skeletal a-actin, and b-myosin heavy chain (Chien et al, FASEB J. 5:3037 (1991)). Similar findings have been reported in vitro after stimulation of Gq-coupled receptors, particularly $a_1$-ARs (LaMorte et al, J. Biol. Chem. 269:13490 (1994)). To determine the effects of the uncoupling of Gq-coupled receptors in vivo, ventricular levels of ANF mRNA were studied by Northern analysis for TG GqI and NLC mice 7 days after sham-operation or TAC. As shown in FIG. 6, basal (sham-operated) ventricular ANF mRNA was nearly undetectable and not different between the two groups. However, after the stimulus of pressure overload, ventricular ANF mRNA in the NLC group increased 6.6-fold while TG GqI animals averaged only a 2.5-fold increase in ventricular ANF mRNA.

All documents cited above are hereby incorporated in their entirety by reference.

One skilled in the art will appreciate from a reading of this disclosure that various changes in form and detail can be made without departing from the true scope of the invention.

TABLE 2

Physiological Parameters in Response to Pressure Overload

| | SHAM | | TAC | |
|---|---|---|---|---|
| | NLC (n = 8) | TG GqI (n = 8) | NLC (n = 10) | TG GqI (n = 18) |
| BW (g) | 20.86 ± 0.73 | 21.40 ± 1.56 | 20.37 ± 0.64 | 22.62 ± 0.78 |
| LV/BW (mg/g) | 3.84 ± 0.30 | 3.72 ± 0.15 | 5.35 ± 0.21* | 4.31 ± 0.12*# |
| SPG (mm Hg) | | | 66.4 ± 7.4 | 62.3 ± 6.8 |

Data expressed as Mean ± SEM. SPG: systolic Pressure Gradient - Difference Between Right and Left Carotid Arterial Systolic Pressure. *P < 0.05 NLC TAC vs. NLC sham; TG GqI TAC vs. TG GqI sham. #P < 0.005 TG GqI TAC vs. NLC TAC (t test).

What is claimed is:

1. A gene expression construct comprising a promoter operably linked to a nucleic acid sequence encoding a Gαq peptide that inhibits Gq-mediated receptor signaling, wherein said peptide comprises the sequence of amino acids from amino acid 305 to amino acid 359 of murine Gαq.

2. The construct according to claim 1, wherein said peptide is the sequence of amino acids from amino acid 305 to amino acid 359 of murine Gαq.

3. The construct according to claim 1, wherein said promoter is a myosin-heavy chain promoter, a CMV promoter, an actin promoter or a myosin light chain promoter.

4. The construct according to claim 1, wherein said construct is naked DNA.

5. A viral vector comprising the construct according to claim 1.

6. The viral vector according to claim 5, wherein the viral vector is a replication-defective retroviral vector, an adenoviral vector or an adeno-associated viral vector.

7. A liposome comprising the construct according to claim 1.

* * * * *